United States Patent
Du Cauze de Nazelle et al.

(12) 
(10) Patent No.: US 6,700,024 B2
(45) Date of Patent: Mar. 2, 2004

(54) PROCESS FOR PREPARING ORGANIC HYDROPEROXIDES

(75) Inventors: Gerard Du Cauze de Nazelle, Jurong Island (SG); Wan Shi Foong, Jurong Island (SG); Tjeerd Willem Garritsen, Moerdijk (NL); Raymond Lawrence June, Jurong Island (SG); Mohammad Azmi Bin Othman, Jurong Island (SG); Eduardus Petrus Simon Schouten, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/247,075

(22) Filed: Sep. 19, 2002

(65) Prior Publication Data

US 2003/0125574 A1 Jul. 3, 2003

(30) Foreign Application Priority Data

Sep. 19, 2001 (SG) ......................... 200105705

(51) Int. Cl.[7] ............................. C07C 409/00
(52) U.S. Cl. ................. 568/571; 568/558; 568/568; 568/569
(58) Field of Search ................ 568/558, 568, 568/569, 571

(56) References Cited

U.S. PATENT DOCUMENTS 5,883,268 A    3/1999   Lin et al. .................... 549/529

FOREIGN PATENT DOCUMENTS

EP         345856      12/1988    ............ B01J/21/06

OTHER PUBLICATIONS

International Search Report, dated Jan. 14, 2003.

Primary Examiner—J. Parsa

(57) ABSTRACT

A process for preparing organic hydroperoxides, which process comprises:

(a) oxidation of an organic compound to obtain reaction product containing organic hydroperoxide,
(b) contacting at least part of the organic hydroperoxide containing reaction product with a basic aqueous solution,
(c) separating hydrocarbonaceous phase containing organic hydroperoxide from aqueous phase,
(d) contacting at least part of the separated hydrocarbonaceous phase containing organic hydroperoxide with an aqueous solution comprising wastewater, and
(e) separating the hydrocarbonaceous phase containing organic hydroperoxide from the aqueous phase.

The invention further relates to a process for preparing an oxirane compounds with the help of this process, and a to a process for preparing an alkenyl aryl with the help of this process.

5 Claims, No Drawings

PROCESS FOR PREPARING ORGANIC HYDROPEROXIDES

FIELD OF INVENTION

The present invention relates to a process for preparing organic hydroperoxides. Such organic hydro-peroxides are suitable for use in various processes, such as in the preparation of oxirane compounds and in the preparation of alkenyl aryl.

BACKGROUND OF THE INVENTION

Processes for preparing propylene oxide employing organic hydroperoxides, are well known in the art. As described in U.S. Pat. No. 5,883,268, such process conventionally comprises peroxidation of ethylbenzene, followed by contacting the peroxidation reaction product with aqueous base in amount sufficient to neutralize acidic components thereof and separating the resulting mixture into an aqueous stream and a deacidified organic stream. The base contaminated, deacidified hydroperoxide stream is washed with water and the resulting mixture separated into an organics contaminated water phase and an organic phase having a reduced alkali metal content. The organics contaminated water phase is contacted with an extractive hydrocarbon and separated into a purified water phase having a reduced level of organic contaminants. It is described that the purified aqueous stream can be discharged with a minimum of further treatment because of its reduced organic impurity level.

From an environmental point of view, it is preferred that the volume of waste streams produced in a process is as small as possible. Further, it is generally more efficient to process wastewater streams containing concentrated organic waste compounds. Therefore, it is preferred that the concentration of organic waste compounds in an aqueous waste stream is high.

It has now surprisingly been found that wastewater, preferably wastewater obtained in one or more process steps of the present process, can be used in the aqueous solution for treating the base contaminated hydroperoxide stream. It has surprisingly been found that the contaminants present in the one or more wastewater streams, do not hamper the cleaning of the hydroperoxide hydrocarbonaceous phase. Furthermore, no negative effect on the performance of the catalyst was observed when the alkyl aryl hydroperoxide containing stream treated with wastewater, was reacted with olefin in the presence of a catalyst as described in EP-A-345856 to obtain alkylaryl hydroxide and oxirane compounds.

SUMMARY OF THE INVENTION

The present invention relates to a process for preparing organic hydroperoxides, which process comprises:

(a) oxidation of an organic compound to obtain reaction product containing organic hydroperoxide,
(b) contacting at least part of the organic hydro-peroxide containing reaction product with a basic aqueous solution,
(c) separating hydrocarbonaceous phase containing organic hydroperoxide from aqueous phase,
(d) contacting at least part of the separated hydrocarbonaceous phase containing organic hydroperoxide with an aqueous solution comprising wastewater, and
(e) separating the hydrocarbonaceous phase containing organic hydroperoxide from the aqueous phase.

Organic hydroperoxides are useful in a range of processes. One of these processes is the reaction of organic hydroperoxide with olefin in order to obtain oxirane compounds. In such process, the organic compound usually is an alkyl aryl, and the process further comprises:

(f) contacting at least part of the hydrocarbonaceous phase containing organic hydroperoxide obtained in step (e) with olefin and catalyst to obtain alkylaryl hydroxide and oxirane compounds, and
(g) separating at least part of the oxirane compound from the alkylaryl hydroxide.

The alkylaryl hydroxide obtained in step (g) can be used in a wide range of processes. Such process is preparing an alkenyl aryl by dehydrating the alkylaryl hydroxide. Another process is hydrogenating the alkylaryl hydroxide to obtain an alkyl aryl. If the process according to the present invention is to be used for dehydrating the alkylaryl hydroxide, the process suitably comprises further:

(h) converting at least part of the alkylaryl hydroxide obtained in step (g). Generally, the conversion produces reaction product and water.

Preferably, step (h) comprises either dehydration or hydrogenolysis of the reaction product. Hydrogenolysis is the reaction of the alkylaryl hydroxide with hydrogen, preferably in the presence of catalyst. Dehydration will generally produce an alkenyl aryl and water, while hydrogenolysis will generally produce alkylaryl. Preferably, the hydrogenolysis will produce the alkylaryl used as starting compound.

DETAILED DESCRIPTION OF THE INVENTION

Although the organic compound used in the process of the present invention can in principle be any compound, organic compounds which are most frequently used are alkylaryl compounds. Alkylaryl compounds which are most frequently used are benzene compounds containing at least about 1 alkyl substituent which alkyl substituent contains of from about 1 to about 10 carbon atoms, preferably of from about 2 to about 8 carbon atoms. Preferably, the benzene compound contains on average of from about 1 to about 2 constituents. The alkylaryl compounds most frequently encountered are ethylbenzene, cumene and di(iso-propyl) benzene.

The oxidation of the organic compound can be carried out by any suitable process known in the art. The oxidation can be carried out in the liquid phase in the presence of a diluent. This diluent is preferably a compound which is liquid under the reaction conditions and does not react with the starting materials and product obtained. However, the diluent can also be a compound necessarily present during the reaction. For example, if the alkylaryl is ethylbenzene the diluent can be ethylbenzene as well.

Besides the desired organic hydroperoxide, a wide range of contaminants are created during the oxidation of organic compounds. Although most of these are present in small amounts, the presence of the organic acids especially has been found to sometimes cause problems in the further use of the organic hydroperoxides. As described in U.S. Pat. No. 5,883,268, the description thereof is herein incorporated by reference, a method of reducing the amount of contaminants is contacting the reaction product containing organic hydroperoxide with an aqueous alkali solution. However, contact with the aqueous alkali solution introduces a certain amount of alkali metal into the organic hydroperoxide containing reaction product. Although the amount of organic acids can be decreased by the alkali wash, the amount of alkali metal contaminants is increased.

In the process of the present invention, the organic hydroperoxide containing reaction product is contacted with a basic aqueous solution, more specifically a basic aqueous solution containing one or more alkali metal compounds. Suitable alkali sources for use in the aqueous alkali solution include alkali metal hydroxides, alkali metal carbonates and alkali metal hydrogen carbonates. Examples of these compounds are NaOH, KOH, $Na_2CO_3$, $K_2CO_3$, $NaHCO_3$ and $KHCO_3$. In view of their easy availability, it is preferred to use NaOH and/or $Na_2CO_3$.

The speed by which the equilibrium is reached in which the majority of the salts of the neutralized alkali metal acids are present in the aqueous phase, can be increased in the ways known to someone skilled in the art. Process step (b) is preferably carried out by intense contacting of the organic hydroperoxide containing reaction product and the basic aqueous solution. Such intense contacting can be done in any way known in the art, for example intense mixing. The exact conditions under which step (b) is carried out, strongly depend on the further circumstances. Preferably, step (b) is carried out at a temperature of between about 0° C. and about 150° C., more preferably of between about 20° C. and about 100° C.

In step (c), the hydrocarbonaceous phase is separated from the aqueous phase. A preferred method comprises allowing the hydrocarbonaceous phase and aqueous phase to settle in a settling vessel and subsequently separating a hydrocarbonaceous phase from an aqueous phase. Preferably, the hydrocarbonaceous phase containing organic hydroperoxide is subsequently sent to a coalescer where further aqueous phase is removed. Preferably, step (c) is carried out at a temperature of between about 0° C. and about 150° C., more preferably of between about 20° C. and about 100° C.

In step (d), at least part of the separated hydrocarbonaceous phase obtained is contacted with an aqueous solution comprising wastewater preferably obtained in one or more process steps of the present process. The aqueous solution comprising wastewater, can be added to separated hydrocarbonaceous phase at any stage after some aqueous phase has been removed from the hydrocarbonaceous phase. A preferred, specific embodiment comprises adding wastewater or aqueous solution containing wastewater to the coalescer used in step (c).

After step (d), the hydrocarbonaceous phase is separated from the aqueous phase in step (e). A preferred method comprises allowing the hydrocarbonaceous phase and aqueous phase to settle in a settling vessel and subsequently separating a hydrocarbonaceous phase from an aqueous phase. The hydrocarbonaceous phase containing organic hydroperoxide is preferably subsequently sent to a coalescer where further aqueous phase is removed. Preferably, step (e) is carried out at a temperature of between about 0° C. and about 150° C., more preferably of between about 20° C. and about 100° C. Further water, unconverted organic compounds and contaminants are preferably separated by distillation from the hydrocarbonaceous phase obtained from the coalescer. Generally, the distillate contains unconverted organic compounds, water and contaminants. The distillate obtained can subsequently be phase separated in a vessel to obtain an organic phase and an aqueous phase. The aqueous phase obtained in this way, will contain organic contaminants and is especially suitable for use as wastewater in step (d).

The aqueous solution as used in step (d) can be any aqueous solution consisting at least partly of wastewater. The aqueous solution can be a combination of fresh water containing substantially no contaminants and one or more different wastewater streams, or it can consist only of different kinds of wastewater streams or it can consist of a single type of wastewater.

Preferably, step (d) comprises contacting at least part of the separated hydrocarbonaceous phase containing organic hydroperoxide, with an aqueous solution comprising both wastewater previously used in washing a hydrocarbonaceous phase containing organic hydroperoxide and a different kind of wastewater. Preferably, the different kind of wastewater is one or more of the specific wastewater streams discussed herein below.

The wastewater previously used in washing a hydrocarbonaceous phase containing organic hydroperoxide, preferably is a wastewater obtained by contacting a hydrocarbonaceous phase containing organic hydroperoxide with an aqueous phase, preferably clean water, and subsequently separating the aqueous phase from the hydrocarbonaceous phase. The aqueous phase so obtained is preferably used as wastewater without further treatment. Most preferably, the wastewater obtained in this way is used in combination with a different kind of wastewater.

The hydrocarbonaceous phase separated and obtained in step (c) is preferably contacted countercurrently with aqueous solution in step (d). Countercurrent operation is considered to comprise contacting with clean water hydrocarbonaceous phase which has already been washed once or more, while contacting hydrocarbonaceous phase which has not yet been washed, with aqueous phase which already has been in contact with hydrocarbonaceous phase. It is preferred to add wastewater to the aqueous solution for treating the hydrocarbonaceous phase which has not yet been washed.

The source of the wastewater for use in step (d) is in principle irrelevant to the present process. However, it is preferred that the wastewater is obtained in a process step related to the present process as this reduces the risk that the compounds present in the hydrocarbonaceous phase react with those present in the aqueous solution. Furthermore, it is preferred not to introduce new components into the process. It has been found that it can be possible to use wastewater containing substantial, amounts of contaminants such as 1,2-propanediol.

In the present invention, it has been found that the presence of contaminants generally do not negatively influence the cleaning of the hydrocarbonaceous phase containing organic hydroperoxide. Furthermore, it has been observed that the presence of contaminants such as organic acids frequently improves the efficiency of the washing of the organic hydroperoxide stream. It was observed that the hydroperoxide stream obtained in step (d) contained less sodium when wastewater containing organic acids had been used in the washing than when solely pure water had been used. Additionally, in many instances an improved separation of the organic and the aqueous phase was observed.

It is surprising that the use in step (d) of an aqueous solution comprising an acidic wastewater, gives good results as the aim of the previous process steps was to remove organic acids which were formed as by-products in the oxidation of step (a). It has now been found that an acidic wastewater can be used in aqueous wash solution of step (d) gives good results without negative impact on a subsequent catalyst such as a catalyst as described in EP-A-345856, the description thereof herein is incorporated by reference.

Wastewater, which has been found especially suitable for use in aqueous solutions for the present invention, is wastewater which is acidic. Preferably, the acidic wastewater comprises one or more organic acids. Organic acids have been found to be generally compatible with the compounds further used in the present process. It is has been found especially preferred if the acid which is present is an organic acid comprising of from about 1 to about 20 carbon atoms. Preferred organic acids to be present in the wastewater include hydrocarbyl carboxylic acids having in total from about 1 to about 10 carbon atoms. Especially preferred acids are formic acid, acetic acid, propionic acid and butyric acid. It has been found that formic acid is especially suitable as formic acid was observed to give only limited decomposition of the organic hydroperoxide.

The concentration of acid in the aqueous solution preferably is from about 0.0001 to about 5% wt, based on total amount of aqueous solution, more preferably from about 0.001 to about 2% wt, most preferably from about 0.001 to about 1% wt.

In step (d), the separated hydrocarbonaceous phase containing hydroperoxide is contacted with the aqueous solution comprising wastewater in order to remove organic contaminants, especially organic salts, more specifically organic alkali salts. Therefore, the aqueous solution comprising wastewater is to be such that treating the hydrocarbonaceous phase containing organic hydroperoxide with the aqueous solution comprising wastewater, reduces the amount of contaminants present in the hydrocarbonaceous phase containing organic hydroperoxide. As a wide range of contaminants might be present in the hydrocarbonaceous phase, it cannot be indicated which compounds are allowable in which amount in the aqueous solution. It will be clear to anyone skilled in the art that it is disadvantageous if the aqueous solution comprising the wastewater contains a high concentration of the contaminants which are to be removed. Preferably, the aqueous solution contains less than about 20% wt of compounds which are to be removed from the organic hydroperoxide containing stream. Preferably, the aqueous solution consists of at least about 80% wt of water, more preferably of at least about 90% wt. The amount of water is preferably at most about 99.99% wt, more preferably at most about 99% wt.

Part of the contaminants will generally have been introduced into the hydrocarbonaceous phase containing organic hydroperoxide by the basic aqueous solution used in step (b). Therefore, it is preferred that the wastewater used in the aqueous solution of step (d) does not contain a substantial amount of basic aqueous solution applied in step (b). Preferably, less than about 10% wt of the basic aqueous solution used in step (b) is used in the aqueous solution of step (d), more preferably less than about 5% wt, most preferably no basic aqueous solution. The amounts are the amounts as present in the process, independent of what amount of these solutions is being recycled. Usually, it is preferred that the aqueous solution comprising wastewater contains less than about 0.2% wt of alkali metal compound and/or salt, based on amount of metal on total amount of solution, preferably less than about 0.1% wt, more preferably less than about 0.05% wt, most preferably less than about 0.01% wt.

Preferably, the total aqueous solution for use in step (d) consists of water and wastewater which aqueous solution has a pH of from about 2 to about 7, preferably of from about 3 to less than about 7, more preferably of from about 3.5 to about 6.5.

Wastewater streams can be used as such. However, in some cases it might be advantageous to concentrate the wastewater stream before use in the process according to the present invention.

Wastewater streams which might be used in step (d) of the present process, are prepared in several ways in the process according to the present invention. Preferred wastewater streams for use in the aqueous solution for use in the present invention contains at least part of one or more of the following wastewater streams: wastewater produced as by-product in the oxidation of organic compound in step (a), wastewater obtained in cleaning filters for off-gas, aqueous distillate obtained by distillation of hydrocarbonaceous phase obtained in step (e) and water obtained in converting alkylaryl hydroxide in step (h). These streams are discussed in more detail herein below.

In the oxidation of the organic compound, it has been observed that water can be produced. It is thought that this water originates from side-reactions such as the decomposition of hydroperoxide. A wastewater stream which can be used in step (d) can be recovered by condensation of the reactor off gas, and separating the hydrocarbonaceous phase. This wastewater stream is especially suitable for use in step (d) in view of its low pH.

In the oxidation of the organic compound, off-gas is produced containing organic contaminants. One of the possibilities to clean this off-gas, is with the help of a filter, more specifically a charcoal filter. The filter has to be cleaned regularly to remove the absorbed contaminants. Usually, this is done with the help of water optionally containing small amounts of further compounds. It has been found that such wastewater obtained in cleaning filters for off-gas is especially suitable for use in the aqueous solution comprising wastewater.

Another wastewater stream which has been found suitable for use in the aqueous solution comprising wastewater, is aqueous distillate obtained by separating hydrocarbonaceous phase from aqueous phase, distilling the hydrocarbonaceous phase and subsequently separating the hydrocarbonaceous distillate from the aqueous distillate. Preferred embodiments for preparing such aqueous distillate for use as wastewater in step (d) have been described above in the discussion of step (e). Such aqueous distillate is especially suitable for use in the aqueous solution used in step (d). Generally, the conversion produces reaction product and water.

A further stream which is especially suitable for use in the aqueous solution is water which is obtained in the conversion of alkylaryl hydroxide of step (h). As mentioned above, the conversion preferably is dehydration or hydrogenolysis. If step (h) comprises dehydration, the product of the dehydration is preferably distilled whereby the distillate obtained contains water and organic compounds. This distillate is phase separated by separating off hydrocarbonaceous phase in a settler and sending the aqueous phase to a coalescer. The aqueous phase obtained in the coalescer van very suitably be used as wastewater in step (d). If step (h) comprises hydrogenolysis, the water produced can be used as wastewater in step (d), preferably after the hydrocarbonaceous phase has been separated off by phase separation. If the hydrogenolysis gives the alkylaryl compound used as starting product, the alkylaryl compound obtained in step (h) is suitably recycled to step (a).

It has been found that in a limited number of instances, an interface emulsion layer or rag is formed upon contacting the hydrocarbonaceous phase containing organic hydroperoxide with the aqueous solution comprising wastewater. Without wishing to be bound to any theory, it is thought that such layer might be formed when a substantial amount of metal, contaminants, such as iron containing compounds, is present. Metal compounds are sometimes present in acidic streams due to corrosion of metal surfaces with which some waste streams have been in contact. Therefore, most conventional methods of removing metal compounds from wastewater are in many cases suitable for preventing rag formation in the present process. Generally, it is preferred that the method is carried out at elevated temperature, preferably at a temperature of at least about 40° C., preferably of at least about 50° C., more preferably of at least about 60° C.

The preferred method of preventing rag formation, is filtration of the wastewater and/or the aqueous solution comprising wastewater. The filter which is preferably used is a filter having openings of about 50 micrometer or smaller, preferably about 30 micrometer or smaller, more preferably about 20 micrometer or smaller.

A further way of preventing rag formation is diluting the wastewater by adding clean water not containing contaminants to the aqueous solution. The amount of clean water to be added depends on the kind and the amounts(s) of contaminants present. It has been found that in many instances, it suffices to add about 30% wt of clean water on total amount of wastewater.

A less attractive option to prevent rag formation, is to distil the wastewater and use the purified wastewater in the aqueous solution.

Dependent on the amount of contaminants present in the hydrocarbonaceous phase containing organic peroxide, process step (d) and (e) can either be carried out once or a number of times. Preferably, the combination of these process steps is carried out of from 1 to 3 times.

In optional process step (f), at least part of the hydrocarbonaceous phase containing organic hydroperoxide obtained in step (e) is contacted with olefin, preferably propene, in the presence of a catalyst to obtain alkylaryl hydroxide and oxirane compounds. A catalyst which can suitably used in such process comprises titanium on silica and/or silicate. A preferred catalyst is described in EP-A-345856, the description thereof is herein incorporated by reference. The reaction generally proceeds at moderate temperatures and pressures, in particular at temperatures in the range of from about 0 to about 200° C., preferably in the range from about 25 to about 200° C. The precise pressure is not critical as long as it suffices to maintain the reaction mixture as a liquid or as a mixture of vapour and liquid. Atmospheric pressure may be satisfactory. In general, pressures can be in the range of from about 1 to about $100 \times 10^5$ N/m$^2$.

The oxirane compounds can be separated from the reaction product containing alkyl aryl hydroxide in any way known to be suitable to someone skilled in the art. The liquid reaction product may be worked up by fractional distillation, selective extraction and/or filtration. The solvent, the catalyst and any unreacted olefin or alkylaryl hydroperoxide may be recycled for further utilization.

The alkylaryl hydroxide obtained in the process can be dehydrated in the presence of a catalyst to obtain styrene and water. Processes which can be used for this step have been described in WO 99/42425, the description thereof is incorporated by reference, and WO 99/42426, the description thereof is incorporated by reference. However, any suitable process known to someone skilled in the art can in principle be used.

The present invention is further illustrated by the following examples.

EXAMPLE 1

In a reactor, air was blown through ethylbenzene. The product obtained contained ethylbenzene hydroperoxide. This product was contacted with a solution containing 0.5% wt NaOH in water and mixed at a temperature of 60° C. The weight ratio of product containing ethylbenzene hydroperoxide to NaOH containing solution was 4.5:1 (wt:wt). The neutralized mixture obtained was sent to a settling vessel where a neutralized hydrocarbonaceous phase containing ethylbenzene hydroperoxide was separated from an aqueous phase.

The neutralized hydrocarbonaceous phase containing ethylbenzene hydroperoxide was sent to a coalescer where further aqueous phase was removed. The neutralized ethylbenzene hydroperoxide solution obtained from the coalescer contained 127 ppm of sodium.

The neutralized hydrocarbonaceous phase containing ethylbenzene hydroperoxide, was washed by mixing the neutralized ethylbenzene hydroperoxide solution from the coalescer with an aqueous solution, separating the mixture obtained in a settling vessel into an aqueous phase and a hydrocarbonaceous phase, subsequently separating the hydrocarbonaceous phase obtained from the settling vessel with the help of a first coalescer, and separating the hydrocarbonaceous phase obtained in the first coalescer with the help of a second coalescer. Each of these steps is described in more detail herein below. The hydrocarbonaceous phase obtained in the second coalescer contains ethylbenzene hydroperoxide, ethyl benzene, water and contaminants. This hydrocarbonaceous phase is distilled. The distillate contains ethyl benzene, water and contaminants. This distillate was phase separated in a vessel to obtain a hydrocarbonaceous phase containing ethyl benzene and contaminants, and an aqueous phase containing water and contaminants. The latter had a pH of 3 and was used as wastewater for use in the aqueous solution for washing the neutralized hydrocarbonaceous phase.

The neutralized ethylbenzene hydroperoxide solution was mixed with an aqueous solution in a ratio of 4.5:1 (wt:wt). The aqueous solution comprised 85% wt of water which is being recycled in this process step to which is added 1.3% wt of clean water and 13.7% wt of wastewater which had been used in washing a hydrocarbonaceous phase containing organic hydroperoxide.

The mixture which was obtained, was sent to a settling vessel where a hydrocarbonaceous phase was separated from an aqueous phase.

NaOH was added to the aqueous phase obtained, which NaOH containing aqueous phase was for use in the neutralization of the hydrocarbonaceous phase containing ethylbenzene hydroperoxide.

The hydrocarbonaceous phase obtained in the settler was sent to a first coalescer, where 1.1 %wt (based on total hydrocarbonaceous phase) of the distillate aqueous phase containing water and contaminants described above, and 1.7 %wt (based on total hydrocarbonaceous phase) of clean water were added. An aqueous phase and a hydrocarbonaceous phase were obtained in the first coalescer. The hydrocarbonaceous phase from the first coalescer was sent to the second coalescer where further 1.4 %wt (based on total hydrocarbonaceous phase) of clean water were added.

The hydrocarbonaceous phase obtained from the second coalescer, was found to contain between 0.1 and 0.2 ppm of sodium.

EXAMPLE 2

Example 1 was repeated except that instead of the distillate aqueous phase containing water and contaminants, a similar amount of clean water was added to the first coalescer.

The hydrocarbonaceous phase obtained from the second coalescer, was found to contain between 0.2 and 0.3 ppm of sodium.

EXAMPLE 3

In a reactor, air was blown through ethylbenzene. The product obtained contained ethylbenzene hydroperoxide. This product was contacted with a solution containing 0.3% wt NaOH in water and mixed intensely at a temperature of 70° C. The weight ratio of product containing ethylbenzene hydroperoxide to NaOH containing solution was 3:1 (wt:wt). The neutralized mixture obtained was phase separated. The neutralized ethylbenzene hydroperoxide solution obtained after phase separation, contained 11.5 mg sodium per kg solution.

The neutralized hydrocarbonaceous phase containing ethylbenzene hydroperoxide, was washed by mixing the neutralized ethylbenzene hydroperoxide solution with an aqueous solution as described below, and phase separating the mixture. This mixing and phase separation, was repeated once. The hydrocarbonaceous phase obtained after phase separation contains ethylbenzene hydroperoxide, ethyl benzene, water and contaminants. This phase is distilled. The distillate obtained contains ethyl benzene, water and contaminants. This distillate is phase separated in a vessel, to obtain a hydrocarbonaceous phase containing ethyl benzene and contaminants, and an aqueous phase containing water and contaminants. The latter had a pH of 3 and was used as wastewater for use in the aqueous solution for washing the neutralized hydrocarbonaceous phase.

The neutralized hydrocarbonaceous phase containing ethylbenzene hydroperoxide, was washed in the following manner. 300 grams of the neutralized ethylbenzene hydroperoxide solution was mixed with 75 grams of the distillate aqueous phase described above. The mixture was shaken for 2 minutes and allowed to settle for 14 minutes. This was carried out at 60° C., and plastic seperation funnels and bottles were used.

The hydrocarbonaceous phase obtained was found to contain less than 0.1 ppm of sodium.

COMPARATIVE EXAMPLE 1

300 grams of the neutralized ethylbenzene hydroperoxide solution as obtained in Example 3, was mixed with 75 grams of clean water having a pH of 7.8. The mixture was shaken for 2 minutes and allowed to settle for 14 minutes. This experiment was carried out at 60° C., and plastic seperation funnels and bottles were used.

The hydrocarbonaceous phase obtained was found to contain 0.1 ppm of sodium.

EXAMPLE 4

In a reactor, air was blown through ethylbenzene. The product obtained contained ethylbenzene hydroperoxide. This product was mixed at a temperature of 70° C. with a solution containing 0.35% wt NaOH and 5% wt of sodium benzoate in dehydration water as described below, and mixed. The weight ratio of product containing ethylbenzene hydroperoxide to NaOH and sodium benzoate containing solution was 4:1 (wt:wt). Subsequently, the mixture obtained was phase separated with the help of a vessel.

The neutralized ethylbenzene hydroperoxide solution obtained contained 8 parts per million weight on weight (ppm) of sodium.

The neutralized solution was subsequently washed with a wastewater stream which was obtained as follows. 1-phenylethanol obtained in a process containing steps (a)–(h) as described above, was converted into styrene. The reaction mixture obtained contained styrene, water, and organic contaminants. The reaction mixture was distilled. This distillate was phase separated. The aqueous phase obtained after phase separation, is hereinafter called "dehydration water" and was used in the washing of the neutralized ethylbenzene hydroperoxide solution. 600 ml of the neutralized ethylbenzene hydroperoxide solution described above was washed with 150 ml dehydration water. The mixture was phase separated.

The hydrocarbonaceous phase obtained after phase separation was found to contain less than 0.05 ppm of sodium.

COMPARATIVE EXAMPLE 2

The process of Example 4 was repeated except in that the dehydration water was replaced by clean water. 600 ml of the neutralized ethylbenzene hydroperoxide solution obtained as described in Example 4, was washed with 150 ml of clean water.

The hydrocarbonaceous phase obtained after phase separation was found to contain 0.12 ppm of sodium.

What is claimed is:

1. A process for preparing alkyl aryl hydroperoxides, which process comprises:
   (a) oxidation of an alkyl aryl compound to obtain a reaction product containing alkyl aryl hydroperoxide,
   (b) contacting at least part of the alkyl aryl hydroperoxide containing reaction product with a basic aqueous solution,
   (c) separating hydrocarbonaceous phase containing alkyl aryl hydroperoxide from aqueous phase,
   (d) contacting at least part of the separated hydrocarbonaceous phase containing alkyl aryl hydroperoxide with an aqueous solution comprising wastewater, and
   (e) separating the hydrocarbonaceous phase containing alkyl aryl hydroperoxide from the aqueous phase.

2. The process according to claim 1, in which process the basic aqueous solution in step (b) contains one or more alkali metal compounds.

3. The process according to claim 1, in which process the wastewater used in the aqueous solution in step (d), is acidic.

4. The process according to claim 1, in which process the wastewater contains one or more organic acids.

5. The process according to claim 1, in which process the aqueous solution comprises wastewater previously used in washing a hydrocarbonaceous phase containing hydroperoxide and a different kind of wastewater.

* * * * *